(12) United States Patent
Kumar et al.

(10) Patent No.: US 6,565,542 B2
(45) Date of Patent: May 20, 2003

(54) EPIDURAL NEEDLE HAVING A DISTAL FLARE

(75) Inventors: Matthew M. Kumar, Oronoco, MN (US); Larry D. Johnson, Red Wing, MN (US)

(73) Assignee: Minnesota High-Tech Resources, Red Wing, MN (US)

( * ) Notice: Subject to any disclaimer, the term of this patent is extended or adjusted under 35 U.S.C. 154(b) by 0 days.

(21) Appl. No.: 09/887,134

(22) Filed: Jun. 22, 2001

(65) Prior Publication Data

US 2002/0198501 A1 Dec. 26, 2002

(51) Int. Cl.[7] .................. A61M 5/00; A61M 25/00; A61M 29/00; A61M 5/178; A61B 17/32
(52) U.S. Cl. ................. 604/264; 604/104; 604/164.01; 604/164.1; 604/272; 604/273; 606/167; 606/185
(58) Field of Search .................. 604/500, 506–507, 604/512, 104, 164.01, 164.1, 164.03, 164.06, 164.09, 264, 272–274; 606/167, 185

(56) References Cited

U.S. PATENT DOCUMENTS

| | | | |
|---|---|---|---|
| 2,904,045 A | 9/1959 | Owings | |
| 4,781,691 A | 11/1988 | Gross | |
| 5,364,373 A | 11/1994 | Waskönig et al. | |
| 5,484,423 A | 1/1996 | Waskönig et al. | |
| 5,843,048 A | 12/1998 | Gross | |
| 5,858,006 A | 1/1999 | Van der AA et al. | |
| 5,938,635 A | 8/1999 | Kuhle | |

FOREIGN PATENT DOCUMENTS

WO  92/07520  5/1992

OTHER PUBLICATIONS

A. van Steenberge, "Sequential Spinal–Epidural Anaesthesia," Journal Fur Anasthesie und Intensivbehandlung; Aug. 2, 1995; pp. 1–3.*

* cited by examiner

Primary Examiner—Gregory L. Huson
Assistant Examiner—Anuradha Ramana
(74) Attorney, Agent, or Firm—Fredrikson & Byron, PA

(57) ABSTRACT

Apparatus and methods for injecting fluid into the epidural space. An improved epidural needle or cannula is provided having a distal bulge or flare located within a few millimeters of the distal tip. The distal flare provides an increased resistance to penetration while the needle is penetrating the ligamentum flavum, and a decrease in resistance to penetration after the distal flare has successfully penetrated the ligamentum flavum. In a preferred embodiment, the distal bulge begins proximally at a distance of less than about 6 millimeters from the distal tip. The epidural needle according to the present invention preferably has the distal bulge or flare beginning proximally at a distance from the distal tip of less than the width of the epidural space. In one method according to the present invention, an epidural needle having a distal flare is advanced to the ligamentum flavum, advanced further through the ligamentum flavum at a perceived higher resistance to travel, until a decrease in resistance to travel is perceived, at which time the distal flare has penetrated the ligamentum flavum into the epidural space, at which time further advancement is stopped.

9 Claims, 4 Drawing Sheets

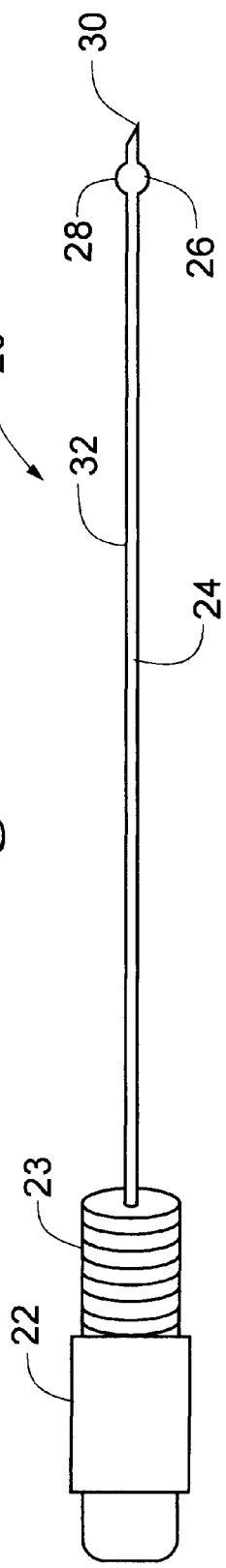
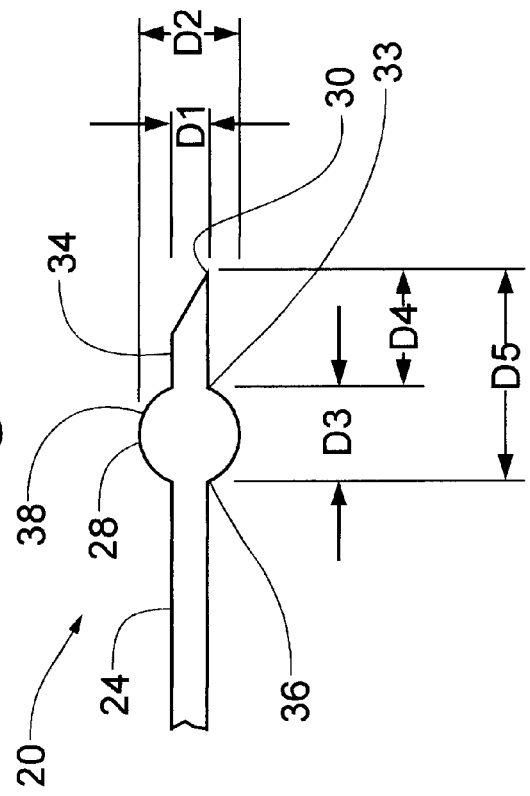
Fig. 1A
Fig. 1B

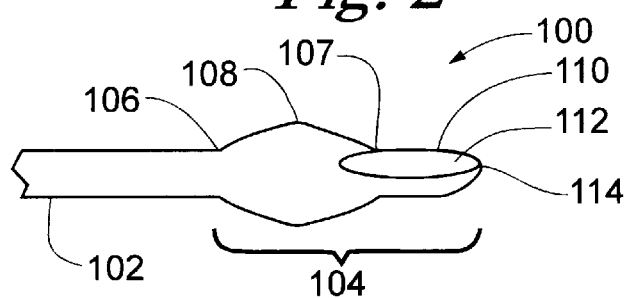
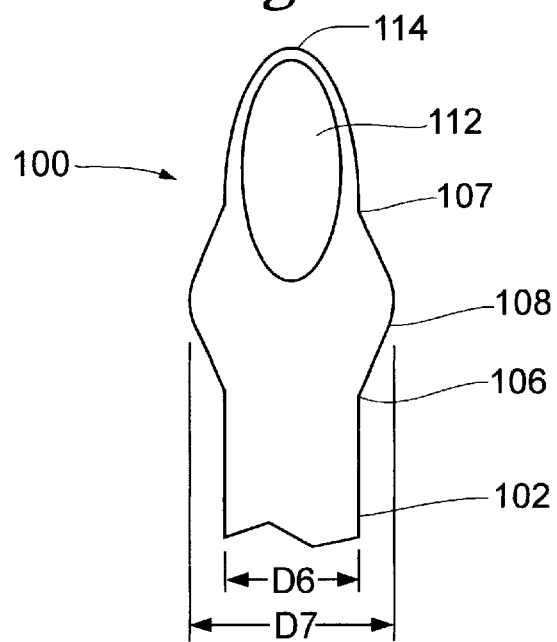
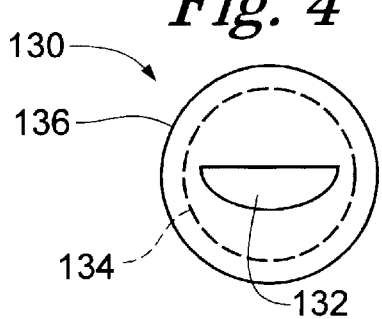
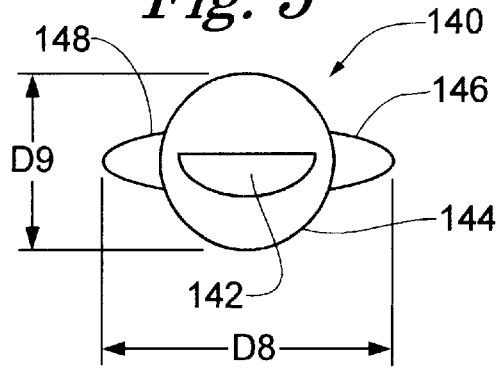

EPIDURAL NEEDLE HAVING A DISTAL FLARE

FIELD OF THE INVENTION

The present invention is related generally to medical devices. More specifically, the present invention is related to epidural needles or cannulas. The present invention includes an epidural needle having a distal flare for providing an increased resistance to penetration, and a greater sense of decrease in resistance to penetration, during and after the needle tip has penetrated the ligamentum flavum, respectively.

BACKGROUND OF THE INVENTION

Injection of fluids into the epidural space involves careful placement of the tip of the epidural needle in the epidural space. Commonly injected fluids include anesthetic agents. Such agents are commonly injected into the epidural space during childbirth to block pain. A plastic catheter may be inserted through the needle into the epidural space and the needle withdrawn for continuous infusion of medications through the catheter. The spinal epidural space is a potential space that extends from the base of the skull to the tail bone or coccyx. Approached from the back, the epidural space is deeper than the ligamentum flavum that connects the vertebral arches, but outside of the dural membrane that covers the spinal cord. This potential space, which varies in width from a few millimeters to a centimeter, normally contains loose areolar tissue, fat, and veins.

It is important to properly locate the epidural space prior to injecting fluid. If the needle penetrates too far, the dural membrane will be punctured, which can result in severe and long lasting headaches. The most commonly used technique to localize, or locate, the epidural space is by testing for the loss of resistance to injection of air or saline. The epidural needle, with a stylet disposed within, is inserted in the midline between the spinous process of two vertebrae and advanced a few centimeters towards the epidural space. Once the needle is embedded in the ligamentous structures, the stylet is removed, and a syringe containing a few milliliters of air or saline is attached to the hub of the needle. The resistance to injection using the syringe is checked either intermittently or continuously as the needle is slowly advanced through the ligamentous structures. Since the tip of the needle is buried in dense ligamentous structures, it will be hard to push the plunger of the syringe. As the needle passes ventral to the ligamrentum flavum, it enters the epidural space and there is a sudden loss of resistance to injected air or saline. A few more milliliters of fluid may be injected to confirm the relatively low pressure in the epidural space.

The epidural space may also be reached through a paramedian puncture. Here the epidural needle is inserted a few centimeters lateral to the midline and advanced towards the epidural space. The needle tip travels through the paraspinous muscles before it punctures the ligamentum flavum. Just as in the midline approach, there will be a loss of resistance to injection of air or saline once the needle tip enters the epidural space. In both the midline approach and the paramedian approach, the loss of resistance to injection of air or fluid is the key to localizing the epidural space.

Another technique described in the literature to localize the epidural space is the "hanging drop" method. (Bromage P R: Epidural Anesthesia. Philadelphia, W B Saunders 1978). A drop of solution is placed within the hub of the epidural needle. When the needle is advanced into the epidural space, the solution is sucked into the shaft of the needle. The theory attributed to this maneuver has been the presence of, or the creation of a subatmospheric pressure in the epidural space by the advancing needle tip. The presence of negative intrathoracic pressure, and the moderate expansion of epidural space by the needle pushing the dura away from the ligamentum flavum, have both been attributed to the low pressure responsible for sucking in the hanging drop.

Either method of localizing the epidural space, the "loss of resistance to injection", or the "hanging drop" technique, relies on identifying the low pressure in the epidural space. Often in clinical practice such identification is not easy. The epidural space is variable in width. Before the surgeon could appreciate the loss of resistance, the needle tip may have crossed the epidural compartment and punctured the dura mater. Dural puncture is undesirable since it leads to complications such as "post dural puncture headache" from loss of cerebrospinal fluid contained within the dural sac. Sometimes the epidural pressure may not be low, from various causes, and as a result, the surgeon may not appreciate the "loss of resistance to injection" being sought. The hollow of the needle may at times get clogged with tissue or a blood clot, further making the perception of low pressure in the epidural space difficult. In addition, pockets of loose areolar tissue or fat, outside the epidural space, may give a false sense of "loss of resistance to injection". This may occur when the needle tip travels from firm tissue, such as a muscle or ligament, into a pocket of loose areolar or fat tissue. This leads to inadvertent injections outside the epidural space.

What would be desirable are improved needles for delivering material into the epidural space which allow for reproducibly locating the epidural space. What would be advantageous are methods for consistently delivering fluids to the epidural space not dependent upon the detection of low fluid pressure within the epidural space.

SUMMARY OF THE INVENTION

The present invention includes apparatus and methods for reproducibly and consistently locating the epidural space for delivery of fluids into the epidural space. The present invention utilizes an important anatomical component, the ligamentum flavum, to locate the epidural space. The ligamentum flavum forms the posterior wall of the spinal epidural space. It is a tough elastic ligament that runs longitudinally, connecting the lamina of adjacent vertebrae. Knowing that this ligament has been punctured informs the surgeon that the needle tip is located within the epidural space. Normally, since the ligamentum flavum is located several centimeters deep to the skin, the intervening ligamentous and muscle tissue render the puncturing of the ligamentum flavum hardly perceptible when using previous needles.

The present invention provides a flare or bulge near the distal tip of the epidural needle, which renders the ligamentum flavum distinctly perceptible to a surgeon as the needle is advanced through the ligament. Immediately after the needle point enters the ligament, the flare or bulge parts the elastic fibers of the ligament widely apart, giving a distinct feel of elastic resistance to the surgeon's fingers advancing the epidural needle. Soon after the flare of the needle tip has passed through the ligament, the elastic fibers of the ligament collapse back around the shaft of a needle. This imparts a sense of "give" or elastic recoil to the surgeon's fingers holding the needle. The creation of a sense of elastic resistance followed by elastic "give" or recoil, as the surgeon advances the epidural needle through the ligamentum flavum, is one aspect of the present invention. The present invention allows the epidural space to be localized irrespective of the pressure in the epidural space. The perception of puncturing the ligamentum flavum signals to the surgeon that the needle has entered the epidural space.

The present invention includes epidural needles having a distal bulge beginning proximally less than about 6 mm., preferable less than about 4 mm. from the distal tip. The present invention also includes methods for advancing an epidural needle, with one method including: providing an epidural needle having a distal tip and a bulge beginning proximally no more than about 4 millimeters from the distal tip; advancing the distal tip distally through the ligamentous structures while sensing a first resistance to advancement; continuing advancing the distal tip as the bulge penetrates the ligamentum flavum while sensing a second resistance to advancement greater than the first resistance to advancement; and stopping further advancement after a decrease in resistance is sensed relative to the first resistance to advancement.

DESCRIPTION OF THE DRAWINGS

FIGS. 1A and 1B are side views of an epidural needle having a distal flare or bulge;

FIG. 2 is a side view of an epidural needle having a distal bulge;

FIG. 3 is a top view of the epidural needle of FIG. 2;

FIG. 4 is an end on view of an epidural needle having a distal bulge formed as a substantially circular, increased radial extent region;

FIG. 5 is an end on view of a needle tip showing the bulge limited to two, opposed, lateral bulges;

DETAILED DESCRIPTION OF THE PREFERRED EMBODIMENT

Figure 6:
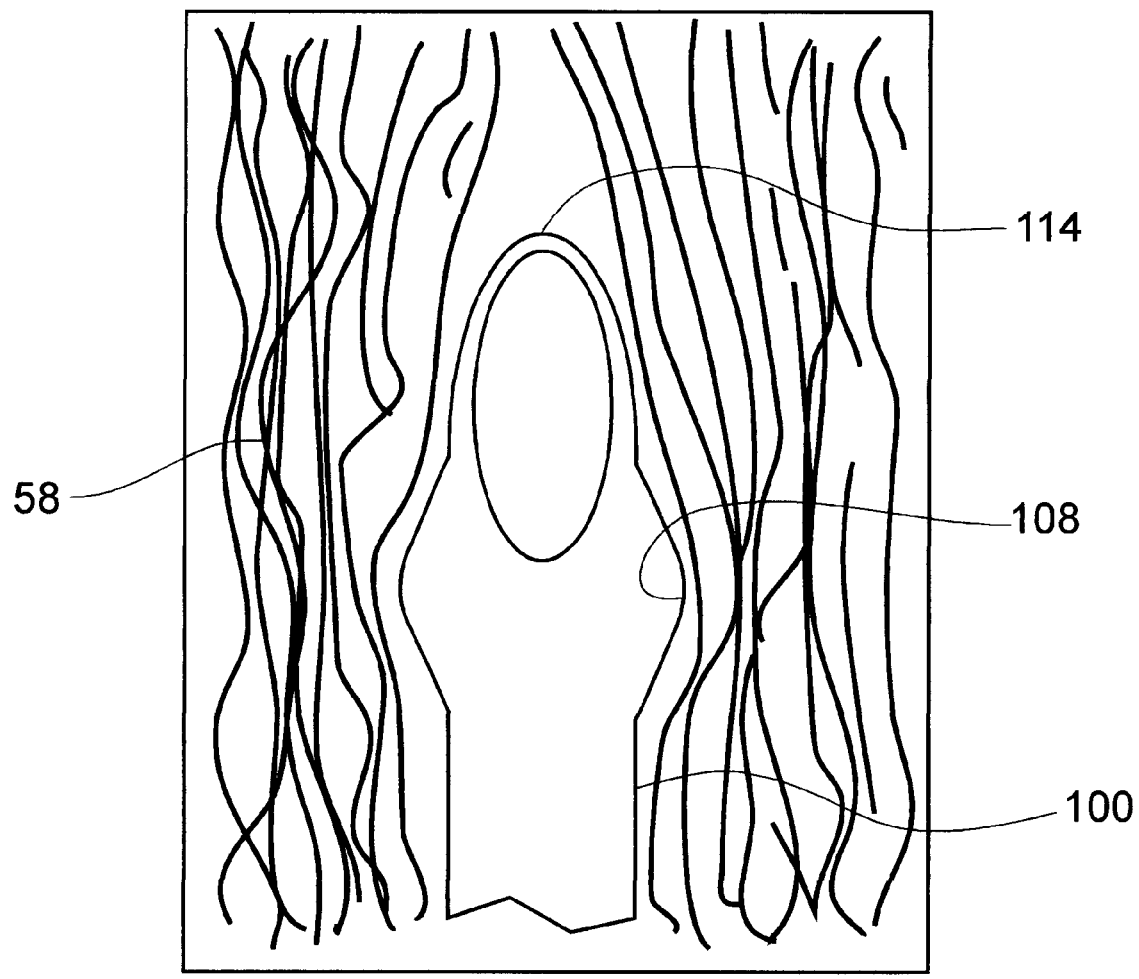
FIG. 6 is a highly diagrammatic representation of an epidural needle tip according to the present invention entering the ligamentum flavum.

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims which follow.

FIG. 1A illustrates an epidural needle 20 having generally a proximal portion 24 and a distal portion 26. Epidural needle 20 includes a proximal hub 22 having a threaded region 23 and a shaft 32. Epidural needle 20 includes within distal portion 26 a distal bulge or flare 28, and terminates in a distal tip 30.

FIG. 1B illustrates epidural needle 20 of FIG. 1A, showing distal portion 26 in greater detail. The region of needle proximal portion 24 immediately proximal of bulge 28 may be hi described as an intermediate region, which may be used as a point at which to measure the needle outer diameter prior to the bulge in some descriptions of the invention. Distal portion 26 includes a distal portion proximal region 38 beginning at 36 and ending distally at 33. Distal portion 26 may be considered to extend from the proximal beginning of the bulge at 36 to distal tip 30. In the embodiment illustrated, distal portion proximal region 38 is occupied entirely by bulge or flared region 28. Distal portion 26 may be seen to have a length indicated by D5, with distal portion proximal region 38 having a length indicated at D3, and the distal portion distal region 34 indicated at D4. In the embodiment illustrated, the needle has a beveled edge which stops distally short of bulge 28, providing a round needle shaft region which is not sharp immediately distal of bulge 28.

In a preferred embodiment, the length from beginning of the bulge at 36 to distal tip 30, indicated as distal portion length D5, has a length sufficient to fit within the width of the epidural space of the intended patient. Thus, length D5 is preferably less than 10 millimeters, more preferably less than about 6 millimeters, and most preferably less than about 4 millimeters. Epidural needle 20 shaft 32 may be seen to have a diameter proximal and distal of bulge 28 as indicated at D1, with bulge 28 having a diameter or maximum transverse extent indicated at D2. Needle shaft 32 may be seen to define a longitudinal dimension, with a transverse dimension being defined orthogonal to the longitudinal dimension. As illustrated in FIG. 1B, bulge 28 has an increased radius or maximum transverse extent indicated at D2, being greater than the shaft diameter indicated at D1. In one embodiment, D2 is less than or equal to 50% greater than D1. D1 may be measured at a point just proximal of bulge proximal beginning point 36. In one embodiment, the D2 size corresponds to a standard 16 gauge needle, while the D1 size corresponds to a standard 18 gauge needle. In some embodiments, bulge 28 is symmetrical about the shaft circumference, being a substantially spherical or cylindrical protrusion. In other embodiments, the bulge or protrusion may be asymmetrical, having discrete protruding elements disposed about the shaft circumference.

FIG. 2 illustrates an epidural needle 100 having a proximal portion 102 and a distal portion 104. Distal portion 104 includes a proximal region having a bulge 108, followed distally by a distal portion distal region 110 having a transversally disposed beveled face 112 disposed therein, terminating distally in a distal tip 114. In the embodiment illustrated, epidural needle 100 has a bulge beginning proximally at 106 and terminating distally at 107.

FIG. 3 illustrates another view of epidural needle 100 of FIG. 2. Epidural needle shaft proximal portion 102 may be seen to have a diameter or transverse extent indicated at D6. Bulge 108 may be seen to have a maximum transverse extent as indicated at D7. The bulge may be seen to begin proximally at 106 and end at 107, with the distal portion terminating distally at tip 114. In one embodiment, the distance from bulge beginning 106 to distal tip 114 is less than 4 millimeters, and can be less than 3 millimeters, to fit within the epidural space. In the embodiment illustrated in FIGS. 2 and 3, beveled face 112 extends proximally into bulge 108, but stops short of extending into the widest region of the bulge.

FIG. 4 illustrates an epidural needle 130 shown in an end on projection view. Epidural needle 130 includes a delivery orifice beveled face 132 disposed within a shaft 134 having the maximum transverse extent or outer diameter indicated at 134. The bulge or increased transverse extent region of epidural needle 130 is indicated by a substantially circular increased transverse extent region 136. FIG. 4 illustrates that the bulge or increased radial extent region can be substantially circular when viewed from the distal end.

FIG. 5 illustrates an epidural needle 140 having a delivery orifice beveled face 142 disposed within a shaft 144 having a diameter or maximum transverse extent indicated at D9. Epidural needle 140 has a bulge or increased transverse extent region formed by a first protrusion or ear 146 and a second protrusion or ear 148. Protrusions 146 and 148 together form an increased transverse extent region or bulge having a width indicated by D8. FIG. 5 illustrates that the protrusion or flare region may be other than circular when viewed from the needle distal end, and may be formed by discrete protrusions or elements.

FIG. 6 illustrates epidural needle 100 having bulge 108 and tip 114 penetrating through the ligamentum flavum 58. In this highly diagrammatic view, tip 114 may be seen to initiate the parting of the ligaments, with bulge 108 providing increased resistance to passage through the ligamentum flavum 58.

Figure 7:
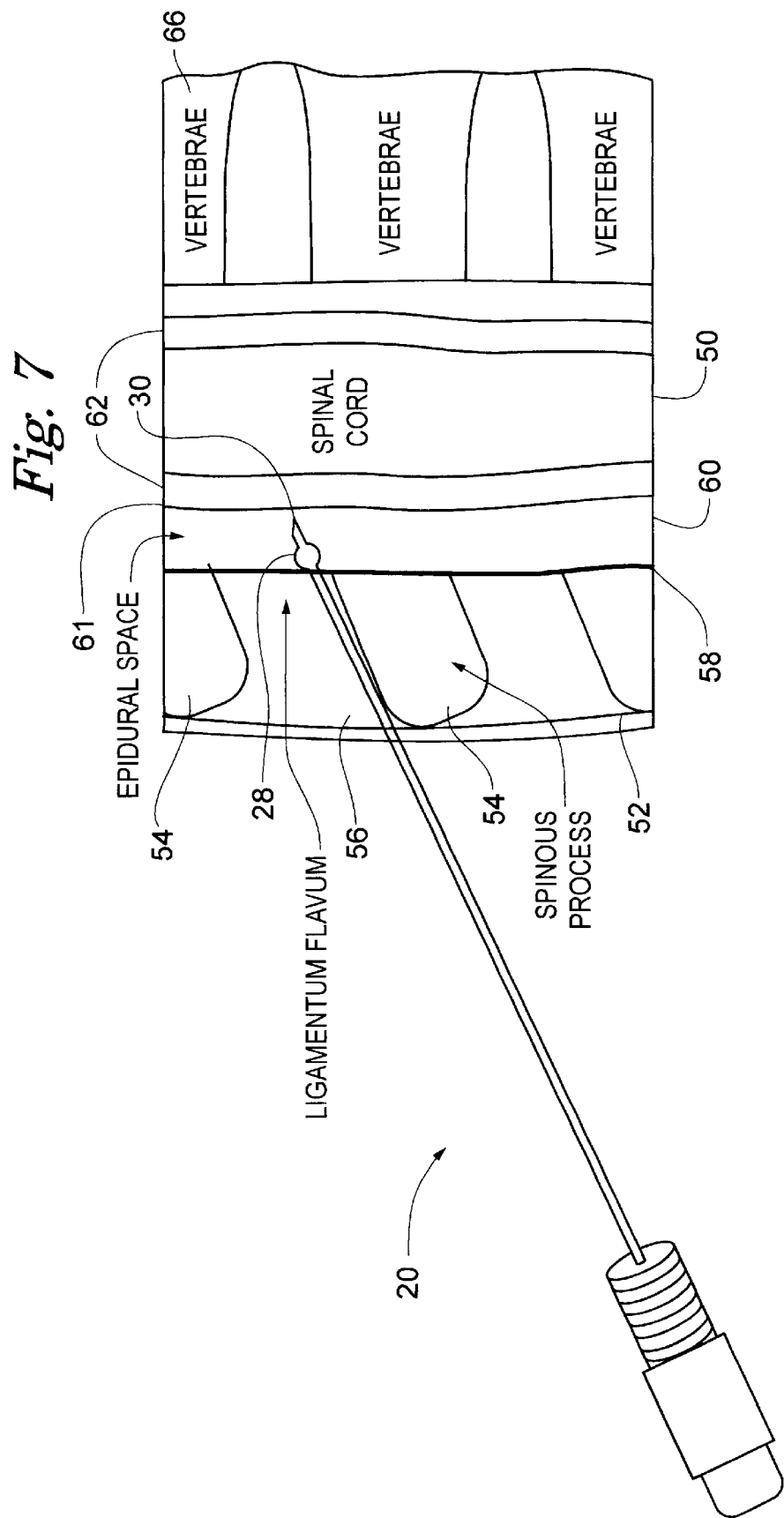
FIG. 7 is a highly diagrammatic illustration of an epidural needle according to the present invention, shown after the distal bulge has penetrated the ligamentum flavum.

FIG. 7 illustrates epidural needle 20 in use. Proceeding from outside in, the skin or epidermis 52 may be seen to cover spinous processes 54 and a ligamentous structures region 56 disposed between spinous processes 54. Ligamentum flavum 58 is illustrated as bounding epidural space 60. The subarachoniod space 62 may be seen disposed about spinal cord 50, followed by vertebrae 66. Epidural needle 20 distal bulge 28 may be seen to have passed through ligamentum flavum 58 and entered epidural space 60 without penetrating into subarachoniod space 62. As may be seen from FIG. 7, the distal tip 30 of epidural needle 20 to would puncture the dura membrane 61 if allowed to proceed further.

Referring again to FIG. 7, a use of the present invention may be further described. The present invention overcomes difficulties inherent in using low pressure to locate the epidural space. Instead, the present invention utilizes the identification of an important anatomical component, the ligamentum flavum, to locate the epidural space. The ligamentum flavum forms the posterior wall of the spinal epidural space. It is a tough, elastic ligament that runs longitudinally connecting the laminae of adjacent vertebrae. Knowing that this ligament has been punctured, the surgeon is assured that the needle tip is located in the epidural space. In prior art devices, as the ligamentum flavum is located several centimeters deep in the skin, the intervening ligamentous and muscle tissue render the puncturing of the ligamentum flavum barely perceptible. The bulge or flare provided at the tip of the present invention renders the ligamentum flavum distinctly perceptible to the surgeon as the needle is advanced through the ligament.

Immediately after the needle distal tip enters the ligament, the bulge or flare parts the elastic fibers of the ligament widely apart, giving a distinct feel of elastic resistance to the surgeon's fingers advancing the epidural needle. Soon after the flare or bulge of the needle tip has passed through the ligament, the elastic fibers of the ligament collapse back around the shaft of the needle. This can impart a sense of give or elastic recoil to the surgeon's fingers holding the needle. The creation of the sense of elastic resistance followed by elastic give or recoil allows the surgeon to reliably and reproducibly locate the epidural needle tip within the epidural space. The perception of puncturing the ligamentum flavum signals to the surgeon that the needle has entered the epidural space.

The resistance offered by the bulge or protrusions of the present invention is proportional to the outer diameter or maximum transverse extent of the bulge. The larger the bulge diameter, the greater the resistance of the needle to the piercing of the ligamentum flavum. The greater the difference between the outer diameter of the bulge and the outer diameter of the needle shaft, the better the appreciation of loss of resistance. In one embodiment, the maximum transverse extent or outer diameter of the bulge is less than 200% of the needle shaft outer diameter. In a preferred embodiment, the outer diameter of the bulge is less than about 150% of the outer diameter of the needle shaft.

In use, an epidural needle is provided, having a bulge beginning proximally within about 6 millimeters, preferable within about 4 millimeters of the distal tip. The epidural needle distal tip is advanced distally to the ligamentous structures and advanced distally through the ligamentous structures while the surgeon senses a first resistance to advancement. The advancing is continued through the ligamentum flavum while the surgeon senses a greater second resistance to advancement as the bulge passes through the ligamentum flavum. After the bulge passes through the ligamentum flavum, the resistance to advancement may drop quite suddenly. The passage of the bulge through the ligamentum flavum may be sensed by the surgeon as an elastic recoil or give. Further advancement of the needle maybe stopped when a decrease in resistance is sensed relative to the second resistance to advancement. In some methods, a small, discrete distance is traversed after the loss of resistance is felt. For example, 1 or 2 millimeters may be advanced after the drop in resistance is sensed. In some methods, however, further advancement is stopped immediately when the loss or decrease in resistance is sensed.

A preferred use of the present invention includes the delivery of material into the epidural space. Anesthetic agents can be injected into the epidural space. The materials can be injected directly through an epidural needle lumen in some methods. In other methods, a catheter may be advanced through the epidural needle lumen and into the epidural space, with the material delivered through the catheter. The present invention may be used to position medical devices generally, including catheters, microcatheters, diagnostic devices, probes, electrodes, and other sensors.

The present invention includes methods for positioning a delivery needle distal tip on the opposite side of a membrane generally. The distal bulge of the present invention may be used to sense the presence of any membrane or other structure that presents a perceptible increase in resistance to travel when crossing into the structure or passing from the structure. In general, the present invention includes apparatus and methods for locating an internal body structure by sensing the change in resistance to travel caused by the body structure interaction with the apparatus distal bulge The present invention may be made of materials commonly used to form epidural needles, well known to those skilled in the art. Any biocompatible, suitable material may be used. The bulge or protrusions in the distal portion may be formed using any suitable method well known to those in the metal working arts. The initial needle may be cast having the bulge. The bulge may be formed in a jig by mechanically grasping the needle on either side of the desired bulge site and causing the needle to buckle slightly as the two gripping sites are brought closer together. Additional metallic material may be added to form the bulge or protrusions. Other needles may have the bulge formed by affixing one or more pieces of material to the outside of a needle. In one embodiment, a cylindrical collar of greater diameter material is slipped over an existing needle and affixed to the existing needle to form the bulge. In one embodiment, the distal portion is flattened somewhat to form an increased transverse extent between the two flattened ears.

What is claimed is:

1. In a patient having ligamentous structures, a ligamentum flavum ventral to the ligamentous structures, and an epidural space ventral to the ligamentum flavum, a method for injecting a material into the epidural space, the method comprising:

providing an epidural needle having a shaft, a lumen therethrough, a distal tip, and a bulge beginning proximally no more than about 6 millimeters from the distal tip;

advancing the distal tip distally through the ligamentous structures while sensing a first resistance to advancement;

continuing advancing the distal tip as the bulge penetrates the ligamentum flavum while sensing a second resistance to advancement greater than the first resistance to advancement;

stopping further advancement after a decrease in resistance is sensed relative to the second resistance to advancement; and injecting the material through the lumen and into the epidural space.

2. A method for injecting material into the epidural space as in claim 1, wherein the stopping farther advancement step includes advancing the distal tip a discrete distance after the decrease in resistance is sensed.

3. A method for injecting material into the epidural space as in claim 2, wherein the discrete distance advanced is less than about 2 millimeters.

4. A method for injecting material into the epidural space as in claim 1, wherein the decrease in resistance is sensed as an increased give in the needle.

5. A method for injecting material into the epidural space as in claim 1, wherein the decrease in resistance is sensed as an elastic recoil.

6. A method for injecting material into the epidural space as in claim 1, wherein the material is injected directly through the epidural needle lumen.

7. A method for injecting material into the epidural space as in claim 1, further comprising providing a catheter having a catheter lumen there through, and advancing the catheter through the needle lumen, wherein the injecting step includes injecting the material through the catheter lumen.

8. In a patient having ligamentous structures, a ligamentum flavum ventral to the ligamentous structures, and an epidural space ventral to the ligamentum flavum, a method for disposing a medical device distal tip into the epidural space, the method comprising:

providing the medical device having the distal tip, a shaft, and a bulge beginning proximally within about 6 millimeters from the distal tip;

advancing the distal tip distally through the ligamentous structures while sensing a first resistance to advancement;

continuing advancing the distal tip as the bulge penetrates the ligamentum flavum while sensing a second resistance to advancement greater than the first resistance to advancement;

stopping further advancement after a decrease in resistance is sensed relative to the second resistance to advancement, such that the medical device distal tip is disposed within the epidural space.

9. In a patient having ligamentous structures, a ligamentum flavum ventral to the ligamentous structures, and an epidural space ventral to the ligamentum flavum, a method for injecting a material into the epidural space, the method comprising:

providing an epidural needle having a shaft, a lumen therethrough, a distal portion, a distal tip, and a bulge disposed in the distal portion;

advancing the distal tip distally through the ligamentous structures while sensing a first resistance to advancement;

continuing advancing the distal tip as the bulge penetrates the ligamentum flavum while sensing a second resistance to advancement greater than the first resistance to advancement;

stopping further advancement after a decrease in resistance is sensed relative to the second resistance to advancement; and injecting the material through the lumen and into the epidural space.

* * * * *